Dec. 13, 1960 E. S. BOERNER Plant Pat. 1,998
ROSE PLANT
Filed March 1, 1960
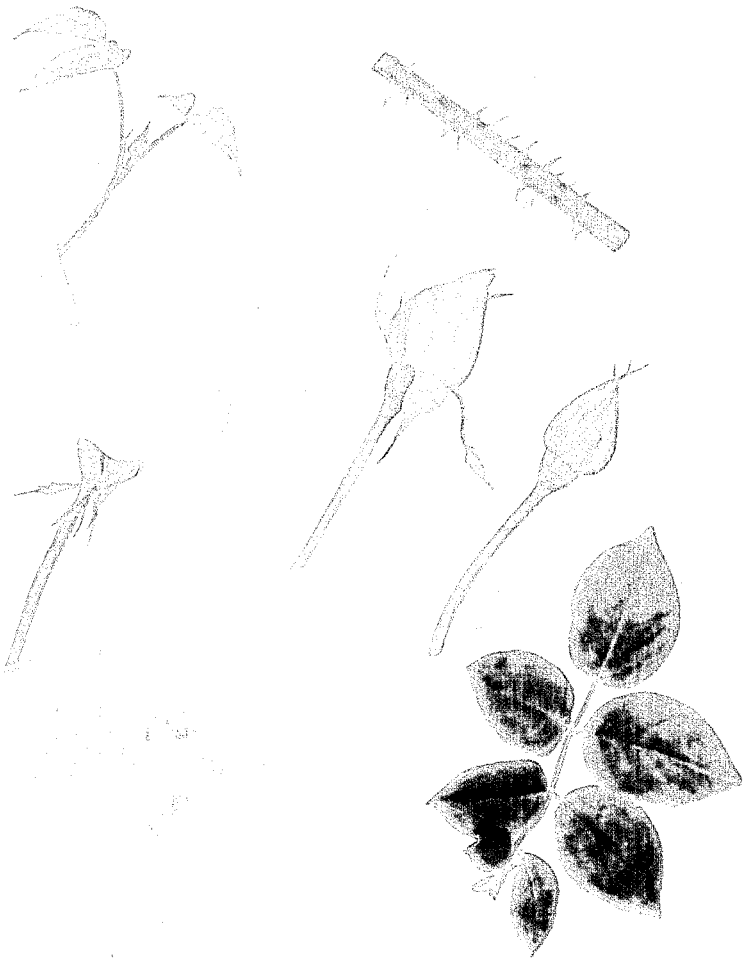
Inventor.
E. S. Boerner
By: Robb & Robb
Attorneys.

United States Patent Office

Plant Pat. 1,998
Patented Dec. 13, 1960

1,998

ROSE PLANT

Eugene S. Boerner, Newark, N.Y., assignor to Jackson & Perkins Company, Newark, N.Y., a corporation of New York Filed Mar. 1, 1960, Ser. No. 12,240

1 Claim. (Cl. 47—61)

The present invention relates to a new and distinct variety of rose plant of the hybrid tea class, which was originated by me by crossing an unnamed and unpatented red seedling with the variety "Peace" (Plant Patent No. 591), said unnamed seedling parent being a variety which was one generation away from the original "Nutneyron" (unpatented) cross of "Paul Neyron" (unpatented) × "Rosa nutkana" (unpatented).

The primary objective of this breeding was to produce a new rose variety having the general characteristics of the variety "Peace," combined with a hardiness substantially greater than that of this patented variety. This objective was fully achieved, along with other desirable improvements, as evidenced by the following unique combination of characteristics which are outstanding in the new variety and which distinguish it from its parents, as well as from all other varieties of which I am aware:

(1) Excellent hardiness (has withstood the most severe winters in northern New York without heavy injury);

(2) A free blooming habit, resulting in the plants being constantly in bloom; and (3) A distinctive and non-fading general color tonality of the flowers corresponding to Thulite Pink, lightly overcast with Spinel Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed red seedling, one generation away from the original "Nutneyron" ("Paul Neyron" × "Rosa nutkana") cross.
- *Pollen parent.*—"Peace."

Classification:
- *Botanic.*—"Hybrid tea."
- *Commercial.*—"Hybrid tea."

*Flower*

(Observations made from specimens grown in a greenhouse at Newark, New York, in the early morning during the early part of the month of April.)

Blooming habit: Recurrent—continuous.

Bud:
- *Size.*—Large.
- *Form.*—Long-pointed; is not affected by wet or hot weather.
- *Color.*—When sepals first divide—Rose Red, Plate 12, lightly overcast with Rose Color, Plate 12.

When petals begin to unfurl—Rose Red, Plate 12, with lower half of the petals lightly overcast with Maize Yellow, Plate 4. When half-blown: inside of petals—Spinel Pink, Plate 26, lightly overcast with Deep Rose Pink, Plate 12; reverse of petals—Deep Rose Pink, Plate 12, lightly overcast with Thulite Pink, Plate 26.
- *Sepals.*—Branched; curl back when petals begin to unfurl. Color: inside—Turtle Green, Plate 32; outside—Light Bice Green, Plate 17.
- *Calyx.*—Color—Bice Green, Plate 17. Shape—pear. Size—long. Aspect—smooth. Odor when rubbed—none.
- *Peduncle.* — Length — medium. Aspect — rough. Strength—erect; heavy. Color—Biscay Green, Plate 17.
- *Opening.*—Opens up well; is not affected by adverse weather conditions.

Bloom:
- *Size.*—Large. Average size when fully expanded—5 inches.
- *Borne.*—Both singly and several together.
- *Stems.*—Medium length; strong.
- *Form (when first open).*—High-centered. Permanence—retains its form to the end.
- *Petalage.*—Double (full but open center). Number of petals under normal conditions—25.
- *Color.*—Center of flower—Spinel Pink, Plate 26, lightly overcast with Deep Rose Pink, Plate 12. Outer petals—Spinel Pink, Plate 26. Base of petals (aiglet)—Chartreuse Yellow, Plate 31. Inside of petals—Thulite Pink, Plate 26, lightly overcast with Spinel Pink, Plate 26. Reverse of petals—Rose Pink, Plate 12, lightly overcast with Thulite Pink, Plate 26. General tonality from a distance—Thulite Pink, Plate 26, lightly overcast with Spinel Pink, Plate 26.
- *Discoloration.*—General tonality at end of first day—Thulite Pink, Plate 26, lightly overcast with Spinel Pink, Plate 26. Second day—Thulite Pink, Plate 26, lightly overcast with Spinel Pink, Plate 26. Third day—Thulite Pink, Plate 26, lightly overcast with Deep Rose Pink, Plate 12.

Petals:
- *Texture.*—Leathery; is not affected by wet or hot weather.
- *Appearance.*—Inside—satiny. Outside—shiny.
- *Form.*—Oval; slightly notched.
- *Arrangement.* — Imbricated (regularly arranged shingle-like).
- *Petaloids in center.*—Few; small.
- *Persistence.*—Drop off cleanly.
- *Fragrance.*—Strong. Nature—"Old Rose perfume" (centifolia).
- *Lasting quality.*—On the plant—long. As cut flower—long.

*Genital organs*

Stamens, anthers: Medium size; many; regularly arranged around styles. Color—Orange Buff, Plate 3.

Stamens, filaments (threads): Long. Color—Venetian Pink, Plate 13.

Pollen: Color—Pale Yellow-Orange, Plate 3.

Styles: Bunched; uneven length; medium length; thin.

Stigmas: Color—Light Pinkish Cinnamon, Plate 29.

Ovaries: All enclosed in calyx.

Hips: None.

Seeds: None.

*Plant*

Form: Bush.

Growth: Vigorous; upright; hardy.

Foliage: Compound of 3 to 7 leaflets.

*Size.*—Large.

*Quantity.*—Normal.

*Color.*—New foliage: upper side — Mignonette Green, Plate 31, with edge of leaves Eugenia Red, Plate 13; under side—Oil Yellow, Plate 5, lightly overcast with Nopal Red, Plate 1. Old foliage: upper side—Forest Green, Plate 17; under side—Light Elm Green, Plate 17.

*Shape.*—Oval pointed.

*Texture.*—Upper side—leathery. Under side—smooth.

*Ribs and veins.*—Prominent.

*Edge.*—Serrated (saw-toothed).

*Serration.*—Single; small.

*Leaf stem.*—Color—Absinthe Green, Plate 31. Under side—prickly.

*Stipules.*—Short; bearded.

Wood:

*New wood.*—Color—Pyrite Yellow, Plate 4. Bark—smooth.

*Old wood.*—Color—Cress green, Plate 31. Bark—smooth.

Thorns:

*Thorns.*—Quantity: on main stalks from base—many; on laterals from stalk—many. Form—narrow base; medium length; hooked downward. Color (when young)—Chamois, Plate 30. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of excellent hardiness, a free blooming habit which results in the plants being constantly in bloom, and a distinctive and non-fading general color tonality of the flowers corresponding to Thulite Pink, lightly overcast with Spinel Pink.

No references cited.